United States Patent [19]

Adams

[11] 3,974,037

[45] Aug. 10, 1976

[54] PROCESS FOR MEASURING CARBON DIOXIDE CONTENT OF THE BODY FLUID

[75] Inventor: Thomas H. Adams, Newark, Del.

[73] Assignee: E. I. Du Pont de Nemours and Company, Wilmington, Del.

[22] Filed: Feb. 1, 1973

[21] Appl. No.: 328,634

[52] U.S. Cl. ........................................... 195/103.5 R
[51] Int. Cl.$^2$ ........................................... G01N 31/14
[58] Field of Search ............................... 195/103.5 R

[56] References Cited
UNITED STATES PATENTS 3,490,874  1/1970  Ando et al. .................. 195/103.5 R

OTHER PUBLICATIONS

Cooper et al., Journal of Biological Chemistry vol. 243 pp. 3857–3863 (1968).
Smith, Archives of Biochemistry and Biophysics vol. 137 pp. 512–522 (1970).

*Primary Examiner*—Alvin E. Tanenholtz

[57] ABSTRACT

A process for measuring the carbon dioxide content of a body fluid comprising the steps of mixing measured amounts of the body fluid with excess amounts of a substrate/enzyme combination selected from the group consisting of
  a. pyruvate and a nucleotide triphosphate/pyruvate carboxylase,
  b. phosphoenol pyruvate/phosphoenol pyruvate carboxylase,
  c. phosphoenol pyruvate and a nucleotide diphosphate/phosphoenol pyruvate carboxy kinase, and
  d. phosphoenol pyruvate and inorganic phosphorous/phosphoenol pyruvate carboxyltransphorylase, and excess amounts of malate dehydrogenase and the reduced form of nicotinamide adenine dinucleotide; and determining the change in the concentration of the reduced form of nicotinamide adenine dinucleotide in the mixture so formed while maintaining the system at a substantially constant temperature and a substantially constant pH.

21 Claims, 1 Drawing Figure

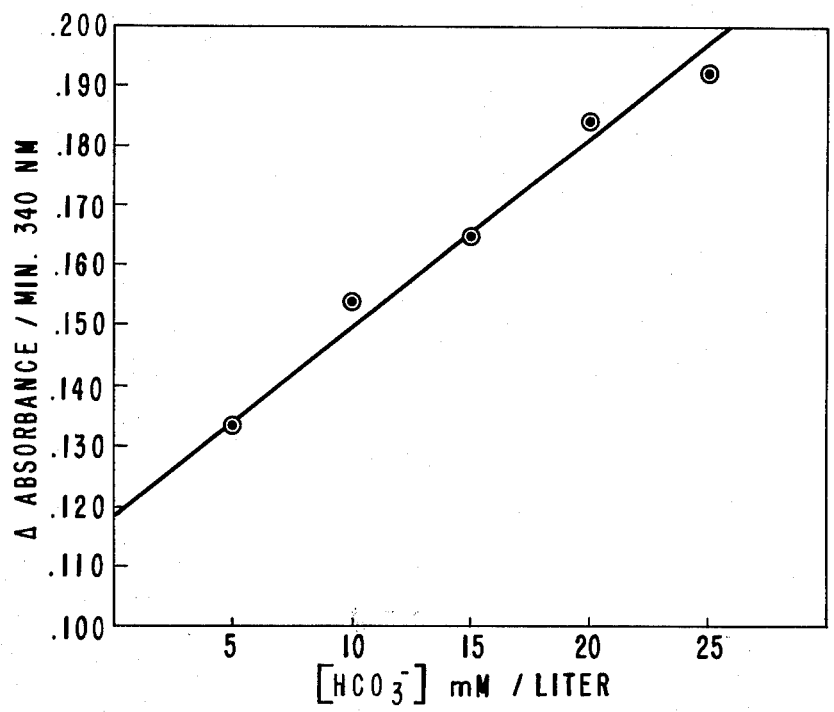

PROCESS FOR MEASURING CARBON DIOXIDE CONTENT OF THE BODY FLUID

BACKGROUND OF THE INVENTION

1. Field of the Invention

This invention relates to a process for the determination of carbon dioxide in a sample, such as a sample of blood serum, and more specifically to a pair of coupled enzymatic reactions for such a determination.

2. Discussion of the Prior Art

The human body generates a large amount of carbon dioxide; only a small portion of which is reutilized, for example, in urea formation or other carboxylation reactions. The rest must be eliminated. One way in which carbon dioxide is eliminated is through the blood stream, and the concentration of carbon dioxide in the blood stream has a profound effect on body function. A moderate elevation in the concentration of carbon dioxide in the blood supply to the brain, for example, greatly enhances cerebral circulation. Abnormal concentrations of carbon dioxide in the blood stream, then, are either the product of or in some circumstances, the cause of a variety of illnesses. For this reason, the measurement of carbon dioxide content in the blood stream or other body fluids is an important measurement in medical diagnostics.

Only a small portion of the carbon dioxide ($CO_2$) introduced into the blood stream remains in the physically dissolved state. The rest is catalyzed into carbonic acid ($H_2CO_3$) by carbonic anhydrase, according to the reaction

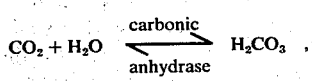

and the carbonic acid is converted into hydrogen ions and bicarbonate ion ($HCO_3^-$) according to the reaction

The term "carbon dioxide content" as it applies to body fluid, actually means the sum of bicarbonate ions, carbonic acid and dissolved carbon dioxide.

The carbonic anhydrase enzyme reaction discussed above has been used to measure the carbon dioxide content of carbonated beverages by adding the enzyme to catalyze the production of carbonic acid and measuring the amount of carbonic acid produced by some indicator, but due to the presence of carbonic acid and the enzyme carbonic anhydrase itself in body fluids, such a process is not appropriate for the measurement of the carbon dioxide content of body fluids. The measurement of the carbon dioxide content in such fluids is usually performed by three basic approaches. In the gasometric approach, $CO_2$ gas is liberated from the serum by the addition of acid, and the volume of $CO_2$ evolved is measured manometrically or volumetrically. Since bicarbonate is a base and produces a pH change when added to weakly buffered solutions, a second approach is to measure the amount of bicarbonate in a sample by measuring the color change in a buffered solution by using an indicator such as phenolphthalein or phenol red. Finally, the partial pressure of $CO_2$ in blood can be measured with a $CO_2$ electrode and the carbon dioxide content can be calculated from this partial pressure if the pH is also measured.

Except for the indicator method, these processes are difficult to automate, especially for use in instruments designed to perform a number of tests by measuring the change in optical absorbance of the test sample. The indicator method, discussed above, suffers from the fact that it must be calibrated every time the measurement is made due to changes in the indicator solution with time. There is need, therefore, for a rapid, reliable, precise process for measuring the carbon dioxide content in a sample, particularly a sample of body fluid, by a method that can be easily automated.

The present invention provides such a process. In its broadest aspect, it comprises the use of one of three coupled enzyme reactions. The preferred reaction is:

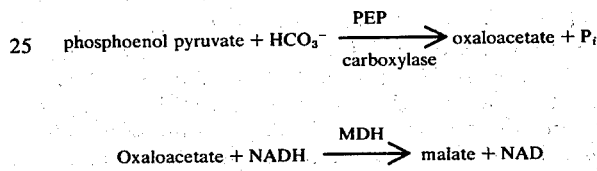

where PEP carboxylase stands for phosphoenol pyruvate carboxylase, $P_i$ stands for inorganic phosphorus, MDH stands for malate dehydrogenase, and NADH and NAD, respectively, stand for the reduced and oxidized form of nicotinamide adenine dinucleotide.

In some circumstances, however, the first of the two reactions given above can be replaced by

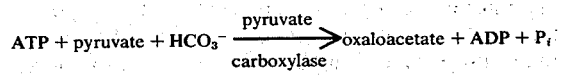

or a reaction involving phosphoenol pyruvate carboxy kinase and a nucleotide diphosphate such as

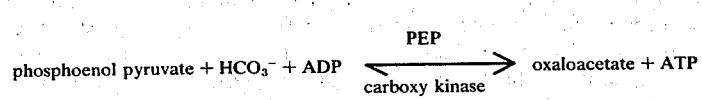

where ADP stands for adenosine disphosphate and ATP stands for adenosine triphosphate, or the following reaction involving phosphoenol pyruvate carboxyltransphorylase and inorganic phosphorous:

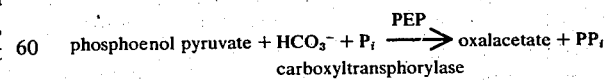

where $PP_i$ stands for inorganic pyrophosphate.

The process comprises mixing measured amounts of body fluid with excess amounts of a substrate/enzyme combination selected from the group consisting of a. pyruvate and a nucleotide triphosphate/pyruvate carboxylase, b. phosphoenol pyruvate/phosphoenol pyruvate carboxylase,
c. phosphoenol pyruvate and a nucleotide disphosphate/phosphoenol pyruvate carboxy kinase, and
d. phosphoenol pyruvate and inorganic phosphorous/puruvate carboxyltransphorylase, and excess amounts of malate dehydrogenase and the reduced form of nicotinamide adenine dinucleotide; and determining the change in the concentration of the reduced form of nicotinamide adenine dinucleotide in the mixture so formed while maintaining the system at a substantially constant temperature and a substantially constant pH.

The term body fluid, as used in this context, means any liquid containing natural products of the body such as an actual body fluid (blood) or a reconstituted body substance (serum).

Each of the above reactions, which actually measure the bicarbonate concentration in a fluid, can be used as a measure of the carbon dioxide content in the fluid because of the equilibrium which exists between $CO_2$ in solution, bicarbonate and carbonic acid. It is well known, however, that carbonic anhydrase will act to convert dissolved $CO_2$ into bicarbonate. See for example the article entitled *The Carboxylation of Phosphoenolpyruvate and Pyruvate* by T. G. Cooper et al. in The Journal of Biological Chemistry, 243, 3857, 1968. For this reason, the accuracy of the test procedures discussed above can be increased by the addition of carbonic anhydrase to the test solution.

Furthermore, each of the reactions discussed above proceed more efficiently if a metal ion cofactor for the enzyme used is present in the reaction mixture to act as a catalyst. Magnesium ions ($Mg^{++}$) or manganese ions ($Mn^{++}$) appear to be common metal ion cofactors in all cases discussed above.

Since the reduced form of nicotinamide adenine dinucleotide absorbs light very strongly between about 290 and about 380 millimicrons, preferably at 340 millimicrons (nm.) while the oxidized form does not, the rate of disappearance of the reduced form is directly proportional to the decrease in absorbance of light at this wavelength and at constant temperature, usually at a constant temperature between 15° and 50°C., and a constant pH, usually between about 7.5 and about 10.5; and can be measured readily by those skilled in the art using a conventional spectrophotometric procedure. Since the rate of oxidation of the reduced form of nicotinamide adenine dinucleotide is also proportional to the rate of formation of oxaloacetate and the rate of formation of oxaloacetate is a function of the concentration of bicarbonate in the system, the decrease in absorbance at 340 millimicrons can be used as a direct measure of the original concentration of bicarbonate in the sample fluid. It should also be understood that other wavelengths, e.g., 366 millimicrons, can be used for the foregoing purpose. Furthermore, the enzyme systems can be coupled with a redox-dye system which will change the wavelength at which the absorbance measurement can be made.

Since blood serum often contains lactate dehydrogenase (LDH) for which pyruvate is a substrate, the process involving pyruvate and pyruvate carboxylase can give an erroneous reading because of the interference provided by this competing reaction, unless the LDH is removed from the sample, or the competing reaction inhibited in some way. For this reason, the reaction involving phosphoenol pyruvate and PEP carboxylase is preferred over that involving pyruvate and pyruvate carboxylase. It is also preferred over the reaction involving phosphenol pyruvate carboxy kinase and a nucleotide diphosphate because it is a simpler reaction involving fewer reagents.

Except for the difference in the compound and its enzyme, the reactions are quite similar. For convenience, the discussion which follows will be limited to the preferred embodiment involving phosphoenol pyruvate and phosphoenol pyruvate carboxylase. As far as this reaction is concerned, it is known that phosphoenol pyruvate carboxylase catalyzes the carboxylation of phosphoenol pyruvate by bicarbonate to oxaloacetate and inorganic phosphate. This reaction has, in fact, been used in conjunction with the malic dehydrogenase indicator reaction to assay the activity of PEP carboxylase, by adding an excess amount of bicarbonate. See *Escherichia coli Phosphoenolpyruvate Carboxylase Characterization and Sedimentation Behavior* by T. E. Smith in the Archives of Biochemistry and Biophysics, 128, 611, (1968). Use has also been made of these two coupled reactions to measure the carbon dioxide concentration in reagents. This latter determination was an end point determination, however, which was allowed to go to completion under a layer of mineral oil.

These coupled reactions, however, have not been used to measure the carbon dioxide content of body fluids. In particular, they have never been used to measure carbon dioxide content by a rate determination. Furthermore, because of the presumed lack of stability of the enzymes used in the determination, and the sensitivity of the process to carbon dioxide which is absorbed into the body fluid from the air rather than from body functions, such processes have generally been discounted for use in automated analysis. I have discovered that an accurate measure of the carbon dioxide content of body fluid can be made using the coupled reactions discussed above. In particular, I have discovered that a rapid and accurate measurement of the carbon dioxide content can be made by using excess non-rate limiting amounts of all constituents, except the body fluid and phosphoenopyruvate carboxylase, and measuring the rate at which the absorbancy of the solution so formed decreases due to oxidation of NADH. I have also discovered that the measurements can be made without fear of inaccuracy introduced by the ambient carbon dioxide level of the air and water if most of the reagents are added to the body fluid in solid form. These solids reagents can be made using a freeze-dry or dry blending technique. Finally, I have discovered that phosphoenol pyruvate carboxylase can be stabilized by the various techniques discussed below.

The production of PEP carboxylase can be carried out according to the techniques described in the article by J. L. Canovas et al. in Biochem Biophys Acta, 96, 189 (166) entitled *Properties and Regulation of Phosphopyruvate Carboxylase Activity in Escherietia coli*, and purified as disclosed in the article by T. E. Smith (supra). In particular, 209 grams of *E. Coli* cells, which had been grown in a Kornberg glucose salt medium, were suspended (30% w/v) in a buffer solution, at a pH of 8.0, composed of 5.0 mM Tris, 1.0 mM magnesium chloride, and 1.0 mM dithioerythritol (DTE). The cells were disrupted by 5 minutes of sonication and the cell debris was removed by centrifugation.

The supernatant, about 500 ml., was pooled and 34 ml. of a 2% solution of protamine sulfate in 5 mM acetate buffer at a pH of 5.0 was added. The precipitate was removed by centrifugation and the supernatant was made 0.4 saturated with $(NH_4)_2SO_4$ by addition of 116 g. of $(NH_4)_2SO_4$. The precipitate was removed by further centrifugation and the supernatant was brought to 0.50 saturation with $(NH_4)_2SO_4$. This precipitate was collected by centrifugation and then dissolved in 15 mls. Tris-Mg-DTE buffer and dialyzed for 12 hours against 2 liters of buffer.

The dialyzed solution was then pumped onto a DEAE cellulose column (2.5 × 40 cm column bed) using a peristaltic pump to maintain a constant flow rate. When the sample was on the column, the column was eluted with a linear chloride gradient by running 0.75 N potassium chloride into the Tris-Mg-DTE buffer. Seven milliliter fractions were collected. The enzyme came off the DEAE cellulose column at a chloride concentration of 0.16 to 0.19 M, and the fractions between 35 and 50 contained a substantial amount of highly active PEP carboxylase.

The enzyme phosphoenol pyruvate carboxylase is an allosteric enzyme and is activated by a number of compounds. Acetylcoenzyme A is the most effective activator however several others, including fructose 1,6 diphosphate, and organic solvents such as ethanol, methanol, propanol and 1,4 dioxane are effective. The reaction mixture should also contain effective amounts of one of those activators.

One of the requirements for the kinetic determination of a substrate is that the enzyme is stable, i.e., the enzyme shows little or no change in activity within the time span of the determination. Furthermore, it is desirable that the enzyme be stable for a reasonable time so that the test material will have a reasonable shelf-life. Studies have shown that the following compositions are useful as stabilizing agents for the enzyme PEP carboxylase.

a.
  0.01 M phosphate
  5.00 mM aspartate
  (pH 7.8)

b.
  0.01 M phosphate
  5.0 mM aspartate
  1.0 mM DTE
  (pH 7.8)

c.
  10% ethanol,
  2.5 mM aspartate d.
  0.1 M phosphate
  2.5 mM aspartate
  25% glycerol
  1.0% albumin
  (pH 7.8)

e.
  50% glycerol
  2.5 mM aspartate
  .01 m phosphate
  1.0 mM $MgCl_2$
  1.0 mM DTE
  (pH 7.8)

f.
  2.05 M $(NH_4)_2SO_4$
  2.5 mM aspartate

Table I shows the effect of these stabilizing agents on compositions studied at 4° and 25°C.

TABLE I

| STABILIZING AGENT | TEMP °C | DAYS | | | | | | | | | |
|---|---|---|---|---|---|---|---|---|---|---|---|
| | | 0 | 1 | 2 | 4 | 7 | 10 | 12 | 14 | 17 | 22 |
| | | % ACTIVITY REMAINING | | | | | | | | | |
| (a) | 4° | 100 | 98 | 98 | 96 | 97 | 97 | | 93 | 89 | |
| | 25° | 100 | 79 | | 4 | 2 | | | | | |
| (b) | 4° | 100 | 98 | 101 | 102 | 101 | 97 | | 92 | 91 | |
| | 25° | 100 | 85 | | 43 | 17 | | | | | |
| (c) | 4° | 100 | 100 | 103 | 105 | 98 | 100 | | 100 | 95 | 96 |
| | 25° | | | | | | | | | | |
| (d) | 4° | 100 | 100 | 103 | 101 | 101 | 98 | | 100 | 100 | 94 |
| | 25° | 100 | 85 | | 25 | 8 | | | | | |
| (e) | 4° | 100 | 100 | 99 | 98 | 97 | 99 | | 96 | 96 | 96 |
| | 25° | 100 | 98 | | 79 | 64 | | 47 | | | |
| (f) | 4° | 100 | 102 | 100 | 105 | 101 | 100 | | 103 | 104 | 109 |
| | 25° | 100 | 98 | | 99 | 97 | | 91 | | | |

All of the compounds have a stabilizing effect, particularly at low temperature storage. The last two, (e) and (f), however, have a marked effect even at room temperature. Preferably, the mixture containing PEP carboxylase will also contain effective amounts of one of these stabilizing agents.

Since carbon dioxide in the atmosphere will permeate the reagents used in the present process and will be converted to bicarbonate as discussed above, for an accurate determination of the carbon dioxide content of body fluid, some attempt must be made to insure that the reagents used are free from atmospheric carbon dioxide. I have found that a blanket of $CO_2$ free nitrogen is effective in reducing $CO_2$ absorption by the solution used in the reaction. Where this is impractical, the buffer and reagents are added as solids, and in order to avoid the problems of $CO_2$ contamination of the reaction solution, the reagents were added as solids to the reaction solution immediately before the reaction.

The reagents used in the assays described in Examples II and III below were prepared as follows:

Malate Dehydrogenase Solution

One ml. of malate dehydrogenase solution (10 mg/ml) was added to 199 ml. of 50% glycerol solution. Fifty microliters of this solution is used per assay.

Tris-Tris-HCl/Mg Buffer Tablets

Tris-Hydroxyaminomethane and Tris Hydroxyaminomethane hydrochloride and $MgSO_4 \cdot 7H_2O$ were sized to −30, to +60 U.S. Standard mesh size. The Tris, Iris HCl and $MgSO_4$ were blended together in a stainless steel pan with a spatula. Polyethylene glycol (PEG 2000) was blended in by hand. This mixture was passed through a No. 20 U.S. Standard mesh screen to disperse the PEG, and then through a No. 30 mesh screen two times to reduce particle size and increase fines content. Eighty milligram tablets were prepared on a Stokes rotary tablet press. Each tablet contained on the average of 43 mg Tris, 22.5 mg Tris HCl, 10.8 mg MgSO₄ and 4.1 mg PEG. One tablet in 5 ml water at 37°C. produces a pH of 8.5.

NADH Tablets

In order to achieve a precise amount of NADH in a tablet, it was necessary to freeze spray the NADH using a Freon Fluorocarbon refrigerant. This requires putting the NADH in an alkaline mannitol solution and spraying. Because of the problem of $CO_2$ pickup by alkaline solutions, the solution was prepared and sprayed under nitrogen pressure. Mannitol (58.40 g) and NADH (disodium salt) (1.60g) were dissolved in 240 ml of purified water under a blanket of nitrogen. When dissolved, the vessel was pressurized with nitrogen and the solution was sprayed into a bath of Freon. The frozen material was collected and lyophilized for 48 hours in a Virtis freeze dryer. The product (47.1 g) was blended with 2.4 g of PEG and 47–48 mg tablets were prepared containing 1.1 mg NADH. One tablet per assay was used.

Phosphoenol Pyruvate Tablets

Phosphoenol pyruvate monocyclohexylammonium salt was blended with Tris, mannitol, PEG in the following amounts: 18 g PEP; 27.6 g Tris; 68.4 g mannitol and 6 g PEG to produce a 100 mg tablet containing 15 mg PEP monocyclohexylammonium salt. One tablet per assay was used.

Phosphoenol Pyruvate Carboxylase Solution

Phosphoenol pyruvate carboxylase was isolated as described above. In Example II, the enzyme was not purified past the ammonium sulfate 30–50% fractionation stage. To 56 ml. of the 30–50% ammonium sulfate cut (26 IU PEP carboxylase/ml.), in the phosphate-asparatate buffer described above, was added 13.5 mg MgSO₄ . 7H₂O and 17.3 mg dithioerythritol. To this solution was added 56 ml glycerol. Sixty-five microliters of this solution was used per assay. This is approximately 0.85 IU per assay.

EXAMPLE I

A kinetic assay of bicarbonate was determined by first preparing a mixture containing

| | |
|---|---|
| phosphoenol pyruvate | 6 mM. |
| PEP carboxylase | 400 mu |
| MgSO₄ | 5 mM. |
| acetyl-coenzyme A | 1 mM. |
| malic dehydrogenase | 10 μg. |
| NADH | 0.125 mM. |
| Tris-HCl | 10 mM. | which is adjusted to a total volume of 2.5 ml. and a pH of 8.5 where mM is millimoles, μg is micrograms and mu is one-thousandth of an enzyme unit. One unit of enzyme is defined as that amount which catalyzes the carboxylation of 1 μM of phosphoenol pyruvate/min. under the conditions of assay.

Using this mixture, a standard curve was generated with bicarbonate standards over the range of 5 millimoles/liter (mM/l) to 25 mM/l. The bicarbonate sample size was 20 μl (microliters). The change in absorbance per minute (ΔAbs/min) in milliabsorbance/min. was measured for each standard. The results are given in Table I.

TABLE I

| BICARBONATE mM/l | ΔA/MINUTE |
|---|---|
| 5 | 134 |

TABLE I-continued

| BICARBONATE mM/l | ΔA/MINUTE |
|---|---|
| 10 | 154 |
| 15 | 165 |
| 20 | 184 |
| 25 | 192 |

FIG. 1 shows the standard curve developed by this work. Good linearity is shown over the range of concentration.

EXAMPLE II

The assay described below was run on the Du Pont Automatic Clinical Analyzer ('aca') using a 20 μl sample in a 5 ml test volume. The reaction was measured kinetically at 340 nm and the analog to digital converter was programmed to readout the results in milli absorbance units/minute. The instrument controls the temperature at 37°C. Eight percent (8%) isopropanol was used as the reaction medium, which also served as an activator for the phosphoenol pyruvate carboxylase.

A standard curve was run on the automatic clinical analyzer (aca) using freshly prepared aqueous sodium bicarbonate standards and analytical test packs with the reagents prepared as described above with 8% isopropanol as an activator. The results of this standard curve are shown in Table II

TABLE II

| BICARBONATE mM/l | ΔA/MINUTE |
|---|---|
| 10 | 122 |
| 20 | 181 |
| 30 | 234 |
| 40 | 286 |

EXAMPLE III

Using the same procedure and reagents set forth in Example II, an analysis of bicarbonate concentration was measured using serum based control products. The manufacturers reported reference values for these products were 10, 25 and 45 mM/l $CO_2$. The results are shown in Table III.

TABLE III

| BICARBONATE mM/l | ΔA/MINUTE |
|---|---|
| 10 | 131 |
| 25 | 213 |
| 45 | 310 |

Using the equation of a straight line, $y = mx + b$, the amount of $CO_2$ present in the serum samples can be calculated from the slope and intercept of the standard curve shown in Table II which as generated using aqueous sodium bicarbonate standards.

In Table IV the results of the calculated $CO_2$ levels in the serum control products as compared to the reference values assigned by the manufacturer are shown.

TABLE IV

| REFERENCE VALUE mM/l $CO_2$ | CALCULATED VALUE mM/l $CO_2$ |
|---|---|
| 10 | 11.32 |
| 25 | 26.25 |

TABLE IV-continued

| REFERENCE VALUE mM/l $CO_2$ | CALCULATED VALUE mM/l $CO_2$ |
|---|---|
| 45 | 44.10 |

These results show good agreement with results obtained by the PEP carboxylase $CO_2$ method and the indicator method used by the manufacturer to assign reference values to the serum.

The same straight line can be used to calculate the $CO_2$ levels in aqueous bicarbonate solutions (i.e., those of Example II).

TABLE V

| REFERENCE VALUE mM/l $CO_2$ | CALCULATED VALUE mM/l $CO_2$ |
|---|---|
| 10 | 9.59 |
| 20 | 20.54 |
| 30 | 30.15 |
| 40 | 39.71 |

The values of $\Delta A$/min. shown in Tables I, II and III are mean values for several replications. In order to assess the precision of the determination, the standard deviation for the values shown in Tables II and III were calculated and converted to mM/l values. Table VI compares the reference values with the mean values and standard deviation for each detection. These are also compared with measurements made on three other commercial devices using data taken from Sterling, R. E., Flores, O. R., Clinical Chemistry 18, 544 (1972).

TABLE VI

PRECISION OF CARBON DIOXIDE ANALYSIS AND METHODS USED

| METHOD AND INSTRUMENT | NUMBER REPLICATES | MEAN mM/l | STD. DEVIATION mM/l |
|---|---|---|---|
| Microgasometer [a] | 45 | 23.3 | 0.74 |
| Technicon 6/60 [b] | 45 | 23.8 | 0.84 |
| Beckman DSA 560 [c] | 45 | 23.5 | 0.88 |
| Du Pont 'aca' [d] | 5 | 9.59 | 0.57 |
| Du Pont 'aca' [d] | 5 | 20.54 | 0.49 |
| Du Pont 'aca' [d] | 5 | 30.15 | 0.35 |
| Du Pont 'aca' [d] | 5 | 39.71 | 0.41 |
| Du Pont 'aca' [e] | 9 | 11.32 | 0.42 |
| Du Pont 'aca' [e] | 9 | 44.10 | 0.32 |
| Du Pont 'aca' [e] | 9 | 26.25 | 0.92 |

[a] - The Microgasometer utilizes a gasometric technique.
[b] - The Technicon 6/60 uses an indicator technique.
[c] - The Beckman DSA uses an indicator method.
[d] - The data is from Table I using the phosphoenol pyruvate carboxylase method on the 'aca' for aqueous bicarbonate standards.
[e] - The data is from Table II using the phosphoenol pyruvate carboxylase method on the 'aca' with serum control products.

It can be seen from Table VI that the phosphoenol pyruvate carboxylase coupled $CO_2$ method measures both aqueous and serum samples with better precision than is attainable by the Microgasometer, Technicon 6/60 or Beckman DSA methods. In only one case was the standard deviation higher for the results run on the Du Pont aca.

The phosphoenol pyruvate carboxylase coupled $CO_2$ method, thus, has the following advantages:

a. The method is both linear and precise, can be calibrated with aqueous bicarbonate standards and measures $CO_2$ in serum accurately and precisely.

b. It is not necessary to standardize the method before each run, since the enzyme has been stabilized so that the calibration curve does not change.

c. $CO_2$ contamination of the reagent system is not a problem, since the reagent system has been put together in such a way to minimize $CO_2$ levels.

What is claimed is:

1. A process for determining the carbon dioxide content of a body fluid which comprises: mixing measured amounts of said body fluid with excess amounts of phosphoenol pyruvate, phosphoenol pyruvate carboxylase, malate dehydrogenase and the reduced form of nicotinamide adenine dinucleotide and measuring the change in the concentration of the reduced form of nicotinamide adenine dinucleotide in the mixture so formed while maintaining the system at a substantially constant temperature and a substantially constant pH of about 7.5 to about 10.5.

2. The process of claim 1 wherein said mixture further comprises a metal ion cofactor for said enzyme.

3. The process of claim 1 wherein said mixture further comprises carbonic anhydrase.

4. The process of claim 1 wherein said nucleotide diphosphate is adenosine diphosphate.

5. The process of claim 1 wherein said mixture further comprises a metal ion cofactor for phosphoenol pyruvate carboxylase.

6. A process for determining the carbon dioxide content of a body fluid which comprises: mixing measured amounts of said body fluid with phosphoenol pyruvate carboxylase and excess non-rate limiting amounts of phosphoenol pyruvate, malate dehydrogenase and the reduced form of nicotinamide adenine dinucleotide; and measuring the rate at which the concentration of the reduced form of nicotinamide adenine dinucleotide in the mixture so formed changes, while maintaining the system at a substantially constant temperature and a substantially constant pH of about 7.5 to about 10.5.

7. The process of claim 6 wherein said mixture further comprises a metal ion selected from the group consisting of magnesium and manganese ions.

8. The process of claim 6 wherein said mixture further comprises a metal ion cofactor for phosphoenol pyruvate carboxylase.

9. The process of claim 7 wherein said mixture further comprises carbonic anhydrase 10. The process of claim 9 wherein the step of measuring the change in concentration of the reduced form of nicotinamide adenine dinucleotide in the mixture is accomplished by measuring the change in the absorbance of the mixture.

11. The process of claim 10 wherein the step of measuring the change in the absorbance of the mixture is accomplished by measuring the decrease in absorbance of the mixture at a wavelength of about 290 nm. to about 380 nm.

12. The process of claim 9 wherein said mixture further comprises effective amounts of stabilizing agent containing ammonium sulfate and aspartate.

13. The process of claim 9 wherein the temperature of the system is maintained at a substantially constant temperature of about 15° to about 50°C.

14. The process of claim 9 wherein said mixture further comprises a measured amount of an activator for the phosphoenol pyruvate carboxylase.

15. The process of claim 14 wherein said activator for the phosphoenol pyruvate carboxylase is acetyl coenzyme A.

16. The process of claim 14 wherein said activator for the phosphoenol pyruvate is an organic solvent selected from the group consisting of ethanol, methanol, propanol and 1,4 dioxane.

17. The process of claim 14 wherein said activator for the phosphoenol pyruvate is fructose 1,6 diphosphate.

18. The process of claim 9 wherein said mixture further comprises effective amounts of a stabilizing agent composed of aspartate, glycerol, phosphate, magnesium chloride and dithioerythritol at a pH of about 7.8.

19. A method for determining the amount of $CO_2$ and $HCO_3^-$ in a sample of blood or blood serum comprising adding phosphoenol pyruvate and an enzyme catalyst selected from the group consisting of phosphoenol pyruvate carboxylase and phosphoenol pyruvate carboxykinase to said sample to cause the reaction of said phosphoenol pyruvate with the bicarbonate ion contained in said sample to produce oxalacetate, and determining the quantity of oxalacetate formed.

20. A method for determining the amount of $HCO_3^-$ in a sample of blood or blood serum comprising adding phosphoenol pyruvate and an enzyme catalyst selected from the group consisting of phosphoenol pyruvate carboxylase and phosphoenol pyruvate carboxykinase to said sample to cause the reaction of said phosphoenol pyruvate with the bicarbonate ion contained in said sample to produce oxalacetate, and determining the quantity of or the rate at which oxalacetate is formed.

21. A process for determining the carbon dioxide content of a body fluid which comprises: mixing measured amounts of said body fluid with phosphoenol pyruvate carboxylase and phosphoenol pyruvate, malate dehydrogenase and the reduced form of nicotinamide adenine dinucleotide; and measuring the rate at which the concenration of the reduced form of nicotinamide adenine dinucleotide in the mixture so formed changes, while maintaining the system at a substantially constant temperature and a substantially constant pH of about 7.5 to about 10.5.

* * * * *